(12) United States Patent
Erbe

(10) Patent No.: US 10,772,685 B2
(45) Date of Patent: Sep. 15, 2020

(54) SYSTEM AND METHOD FOR BONE RE-REGISTRATION AND MARKER INSTALLATION

(71) Applicant: THINK SURGICAL, INC., Fremont, CA (US)

(72) Inventor: Klaus George Erbe, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 366 days.

(21) Appl. No.: 15/869,651

(22) Filed: Jan. 12, 2018

(65) Prior Publication Data

US 2018/0200001 A1    Jul. 19, 2018

Related U.S. Application Data

(60) Provisional application No. 62/446,719, filed on Jan. 16, 2017.

(51) Int. Cl.
*A61B 34/20* (2016.01)
*A61B 90/00* (2016.01)
*A61B 17/00* (2006.01)

(52) U.S. Cl.
CPC ............ *A61B 34/20* (2016.02); *A61B 90/39* (2016.02); *A61B 2017/00115* (2013.01); *A61B 2034/207* (2016.02); *A61B 2034/2051* (2016.02); *A61B 2034/2055* (2016.02); *A61B 2034/2059* (2016.02); *A61B 2034/2063* (2016.02); *A61B 2090/363* (2016.02); *A61B 2090/3916* (2016.02); *A61B 2090/3987* (2016.02)

(58) Field of Classification Search
CPC ..................................................... A61B 34/20
See application file for complete search history.

(56) References Cited

U.S. PATENT DOCUMENTS

| | | | |
|---|---|---|---|
| 5,086,401 | A | 2/1992 | Glassman et al. |
| 5,951,475 | A | 9/1999 | Gueziec et al. |
| 6,033,415 | A | 3/2000 | Mittelstadt et al. |
| 6,061,644 | A | 5/2000 | Leis |
| 6,322,567 | B1 | 11/2001 | Mittelstadt et al. |
| 6,430,434 | B1 | 8/2002 | Mittelstadt |
| 7,043,961 | B2 | 5/2006 | Pandey et al. |

(Continued)

FOREIGN PATENT DOCUMENTS

WO    2017151751 A1    9/2017

*Primary Examiner* — Rochelle D Turchen
(74) *Attorney, Agent, or Firm* — Blue Filament Law PLLC

(57) ABSTRACT

A process and system are provided for placing recovery markers on a bone, prior to surgery, at locations that permit the bone to be re-registered within a desired degree of accuracy. The process includes installing a first recovery marker on the bone, and digitizing a first position with a digitizer probe having a probe tip. Subsequently, a user navigates along a surface of the bone with the probe tip to place a second recovery marker on the bone. A processor calculates a distance between the first recovery marker and the probe tip, and notifies a user when the processor calculates that a probe tip position is at or beyond a pre-determined distance from the first recovery marker. A second recovery marker is installed on the bone at or beyond the pre-determined distance, and is digitized to permit bone re-registration using the first recovery marker and the second recovery marker.

20 Claims, 7 Drawing Sheets

(56) References Cited

U.S. PATENT DOCUMENTS

| | | |
|---|---|---|
| 7,206,626 B2 | 4/2007 | Quaid, III |
| 8,287,522 B2 | 10/2012 | Moses et al. |
| 8,876,830 B2 | 11/2014 | Hodorek et al. |
| 8,961,536 B2 | 2/2015 | Nikou et al. |
| 2005/0216032 A1 | 9/2005 | Hayden |
| 2006/0142657 A1* | 6/2006 | Quaid ............... A61B 17/1675 600/424 |
| 2011/0208093 A1* | 8/2011 | Gross ................. A61B 5/4528 600/587 |
| 2013/0060278 A1 | 3/2013 | Bozung et al. |
| 2014/0039517 A1 | 2/2014 | Bowling et al. |
| 2017/0258532 A1 | 9/2017 | Shalayev et al. |
| 2018/0014888 A1 | 1/2018 | Bonny et al. |

\* cited by examiner

SYSTEM AND METHOD FOR BONE RE-REGISTRATION AND MARKER INSTALLATION

CROSS-REFERENCE TO RELATED APPLICATION

This application claims priority of U.S. Provisional Patent Application Ser. No. 62/446,719 filed Jan. 16, 2017, which is incorporated herein by reference.

TECHNICAL FIELD

The present invention generally relates to the field of computer-assisted orthopedic surgery, and more particularly to a new and useful method for placing recovery markers on a bone, prior to surgery, at locations that permit the bone to be re-registered within a desired degree of accuracy.

BACKGROUND

Throughout a lifetime, bones and joints become damaged and worn through normal use, disease, and traumatic events. Arthritis is a leading cause of joint damage that leads to cartilage degradation, pain, swelling, stiffness, and bone loss overtime. Arthritis can also cause the muscles articulating the joints to lose strength and become very painful.

If the pain associated with the dysfunctional joint is not alleviated by less-invasive therapies, a joint arthroplasty procedure is considered as a treatment. Joint arthroplasty is an orthopedic procedure in which an arthritic or dysfunctional joint surface is replaced with an orthopedic prosthesis.

The accurate placement and alignment of an implant is a large factor in determining the success of joint arthroplasty. A slight misalignment may result in poor wear characteristics, reduced functionality, poor clinical outcomes, and decreased prosthetic longevity.

In order to achieve accurate implant placement and alignment, the cutting tool must be accurately positioned relative to the bone prior to making any bone cuts and/or modifications. In some methods, a cutting jig may be used to accurately position and orient a cutting tool such as a saw, drill, or reamer. In other methods, the cuts may be made using a computer-assist device (e.g., a surgical robot) that controls a saw, cutter, or reamer. When a computer-assist device is used to make the cuts, the bone's position and orientation (POSE) must be known precisely in three-dimensional space (and hence relative to the computer-assist device) to ensure that the cuts and/or modifications are made in the correct location. Several methods to determine the POSE of a bone relative to a computer-assist device are known in the art such as the registration methods described in U.S. Pat. Nos. 6,033,415 and 5,951,475.

However, bone motions during the process of cutting and implant replacement may generate cutting inaccuracies during the bone surgery if the bone is fixed with respect to the computer-assist device and not tracked in 6-DOF by a tracking system where the registration may otherwise be updated as the bone moves. Should a sufficient amount of bone motion occur, it is then necessary to immediately stop the cutting operation and restart the cutting procedure after re-registering the position of the bone with respect to the computer-assist device. Additionally, if a 6-DOF tracking system is used to update the registration as the bone moves, the tracking device (e.g., a tracking array of an optical tracking system) attached to the bone may still move relative to the bone after the initial registration, in which case the 6-DOF tracking is no longer valid and bone re-registration is still required.

In order to facilitate the process of restoring the registration after bone motion occurs, a system and method using recovery markers placed on the bone may be employed as described in U.S. Pat. No. 6,430,434. These recovery markers can be used to quickly re-register the bone by re-digitizing the location of the recovery markers.

In order to accurately resolve six degrees of freedom (6-DOF) of bone motion to recover the registration, the recovery markers must be placed a certain distance apart. In general, as the distance between the recovery markers increases, the accuracy in resolving 6-DOF also increases. Thus, there is typically a lower limit distance, either pre-determined experimentally, mathematically, or via simulations, in which the recovery markers must be distanced apart to accurately resolve all 6-DOF. This lower-limit distance is referred to herein as the "pre-determined distance". Currently, the installation of the recovery markers is accomplished by a user installing a first recovery marker on the bone using a standard surgical drill. After the first recovery marker is installed, the user is either guessing where to place a subsequent recovery marker in the bone to satisfy the pre-determined distance, or a physical ruler is used to measure the pre-determined distance. However, this method is very time consuming and frustrating for the surgical team. In addition, there is often limited exposure of the bone, making it even more difficult to find a suitable location for any subsequent recovery marker that also satisfies the pre-determined distance.

Thus, there is a need for a more efficient method for determining an accurate location for a subsequent recovery marker to permit a re-registration of a bone within a desired accuracy.

SUMMARY OF THE INVENTION

A process is provided for preparing a bone for re-registration prior to surgery. The process includes installing a first recovery marker on the bone, and digitizing a first position of the first recovery marker with a digitizer probe having a probe tip. Subsequently a user navigates along a surface of the bone with the probe tip to search for a position to place a second recovery marker on the bone while a processor calculates a distance between the first recovery marker and the probe tip. The user is notified when the processor calculates that a probe tip position of the probe tip is at or beyond a pre-determined distance from the first recovery marker. A second recovery marker is installed on the bone at or beyond the pre-determined distance, and a second position of the second recovery marker is digitized to permit bone re-registration using the first recovery marker and the second recovery marker.

A system is provided for implementing a method of re-registration of a bone during a surgical procedure. The system includes a robot configured with a digitizer probe to implement measurements for bone registration, and one or more computers having one or more processors for calculating the distance between the probe tip and a first recovery marker.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 4A depicts a visual signal, FIG. 4B depicts an audible signal, and FIG. 4C depicts a haptic signal in accordance with embodiments of the invention;

DETAILED DESCRIPTION

Figure 1:
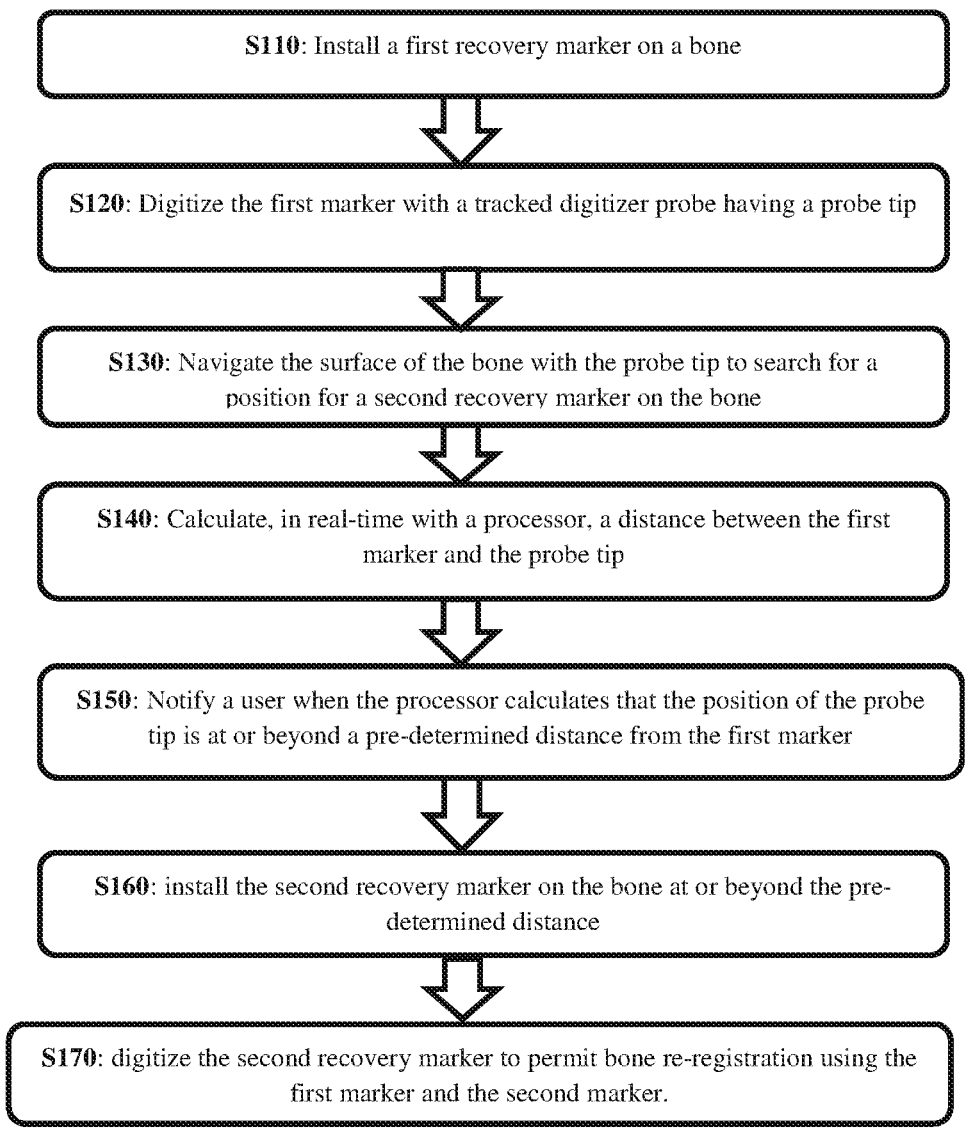
FIG. 1 is a flowchart depicting a method for determining a location for a second recovery marker to permit a re-registration of a bone within a specified accuracy according to embodiments of the invention.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Definitions

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "registration" refers to the determination of the spatial relationship between two or more objects or coordinate systems such as a computer-assist device and at least one of a bone, or an image data set of a bone. "Re-registration" refers to any subsequent registration procedure that occurs after an initial registration and is executed with the use of the recovery markers.

As used herein, the term "digitizer" refers to a measuring device capable of measuring physical coordinates in three-dimensional space. Examples of a "digitizer" include: a high-resolution electro-mechanical sensor arm as described in U.S. Pat. No. 6,033,415 such as a robotic arm, a mechanical digitizer, or a 6-DOF mechanical tracking systems; an optical tracking system tracking an optically trackable probe as described in U.S. Pat. No. 7,043,961; electro-magnetic tracking systems; ultrasound tracking systems; and/or an imaging system (e.g., computed tomography (CT), X-ray, fluoroscopy, ultrasound, magnetic resonance imaging (MRI)), and similar measuring devices and systems known in the art.

As used herein, the term "recovery marker" refers to a physical reference marker designed to permit a measurement system such as a digitizer to determine at least one of a position or orientation of at least a portion of the reference marker.

As used herein, the term "pre-determined distance" refers to a distance between two or more recovery markers sufficient to re-register the bone (i.e., resolve the motion of an object or a targeted region of an object in 6-DOF) within a desired accuracy. The ability to re-register the object to a desired accuracy is a function of many factors including the size of the object, the expected motion of the object, the signal to noise ratio of the digitizer measurements, the variability of how a user might digitize the same points on the recovery markers, the inherent variability or error of the digitizer measurements, the algorithms performing the re-registration computational steps, the type of surgical system, as well as other factors. However, one of skill in the art may assess each of these variables to determine the pre-determined distance necessary to achieve a desired accuracy, where the desired accuracy is highly dependent on the application. In specific embodiments, for computer-assisted total joint replacement (TJR) surgery, the desired accuracy is very high such that the final implant placement does not shift by more than 1 mm in translation and 1° in rotation due to re-registration and preferably less. For human hip and knee replacement surgeries involving the femur, tibia, and pelvis, it was determined experimentally that this accuracy may be achieved if the distance between the recovery markers is at least 35 mm or greater. It should be appreciated however, that the 35 mm distance is highly dependent based on the factors described above and is therefore not limiting unless expressly claimed in the claims following the specification.

As used herein, the term "digitizing" refers to the collection, recordation, or measurement of one or more physical coordinates in three-dimensional space.

As used herein, the term "real-time" refers to processor in which input data is processed within milliseconds such that calculated values are available within 10 seconds of computational initiation.

Also, referenced herein are computer-assisted surgical systems. Examples of surgical systems illustratively include a 1-6 degree of freedom hand-held surgical system, a navigated surgical system, a serial-chain manipulator system, a parallel robotic system, or a master-slave robotic system, as described in U.S. Pat. Nos. 5,086,401, 6,033,415, 7,206,626, 8,876,830 and 8,961,536, U.S. Pat. App. Nos. 2013/0060278 and 2005/0216032, and U.S. Prov. App. No. 62/054,009 all of which are incorporated by reference herein in their entirety. The computer-assisted surgical system may provide autonomous, semi-autonomous, haptic, or no (passive) control, or any combination thereof.

While the present invention is illustrated visually hereafter with respect to a femur as the bone for which positional registry has been lost and to which the present invention is applied, it is appreciated that the present invention is equally applicable to other bones of a human, non-human primate, or other mammals.

With reference to the figures, FIG. 1 generally depicts a method 100 for installing a plurality of recovery markers on a bone a sufficient distance apart prior to surgery, to permit bone re-registration within a desired accuracy following bone motion. A first recovery marker is installed on the exposed bone (S110), and digitized with a tracked digitizer probe having a probe tip (S120). A user, with the digitizer probe, navigates the surface of the exposed bone with the probe tip to search for a location for a second recovery marker to be installed on the bone (S130). A processor, in some inventive embodiments in real-time, calculates the distance between the probe tip and the first recovery marker as the user navigates the surface of the bone (S140). A feedback mechanism then notifies the user when the processor calculates that the probe tip is at or goes beyond a pre-determined distance from the first marker (S150). This notification signals an adequate position for the installation of a second recovery marker that in combination with the first recovery marker position permits the bone to be re-registered within a desired accuracy. The user may then install a second recovery marker at or beyond the position of the probe tip (S160), or continue searching for another adequate position for the installation of a second recovery marker that satisfies the pre-determined distance. After the second recovery marker is installed on the bone, the user digitizes the second marker to permit bone re-registration as needed during a pause in surgical procedure as necessary (S170). With bone re-registry a surgical procedure can again resume. Specific embodiments of the method and components are further described in detail below.

Figure 2A:
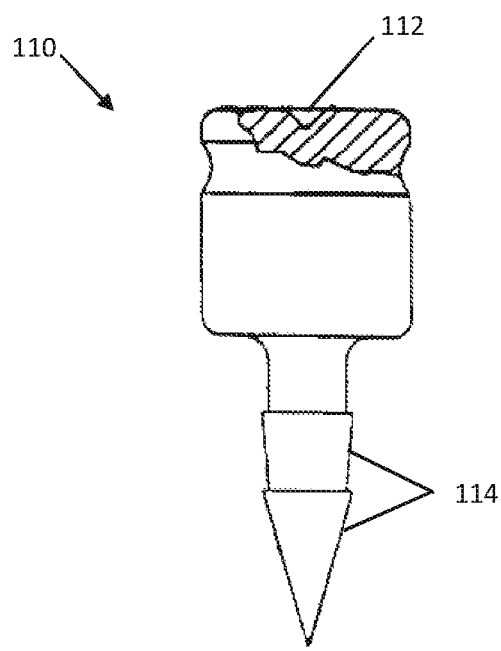
FIG. 2A depicts a prior art point recovery marker.
Figure 2B:
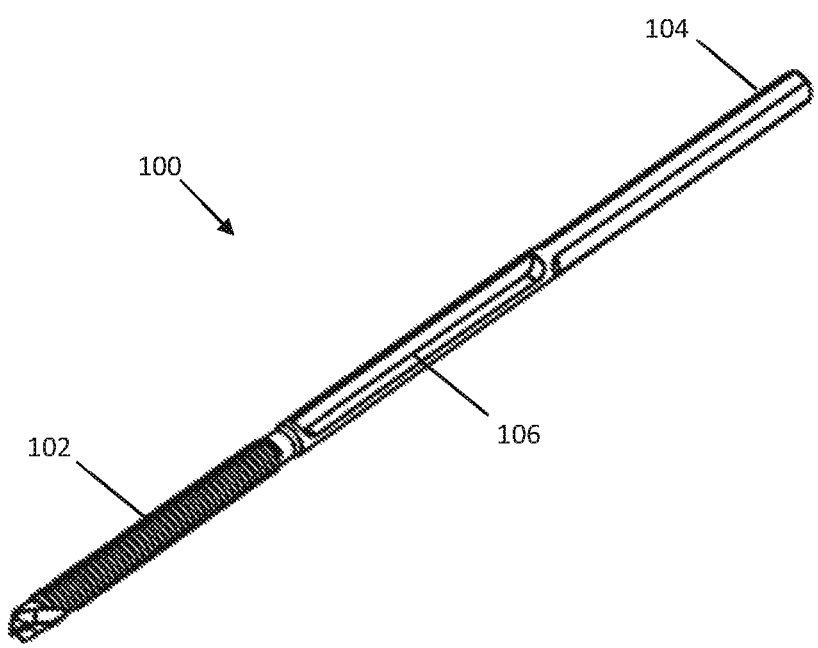
FIG. 2B depicts a prior art groove recovery marker.

FIG. 2A depicts an example of a prior art point recovery marker 110 as described in U.S. Pat. No. 6,430,434. The point recovery marker 110 includes a divot 112 for facilitating the collection of a fixed point, and a bone engaging portion 114 for engaging a bone. FIG. 2B depicts an example of a prior art groove recovery marker 101. The groove recovery marker 101 includes a bone engaging portion 102, a proximal portion 104, and a groove 106 between the bone engaging portion and the proximal portion 104. The bone engaging portion 102 may include threads or flutes to grasp the bone. A driver tool, such as a screwdriver or drill, may receive the proximal portion 104 to aid in driving the groove recovery marker 101 into the bone. The groove 106 facilitates the collection of a series of points along the length of the groove 106. A method for re-registering a bone using the point recovery marker 110 and groove recovery marker 101 is described in U.S. Prov. Pat. App. 62/302,733 filed Mar. 2, 2016 that is assigned to the assignee of the present application and incorporated by reference herein in its entirety.

Figure 3A:
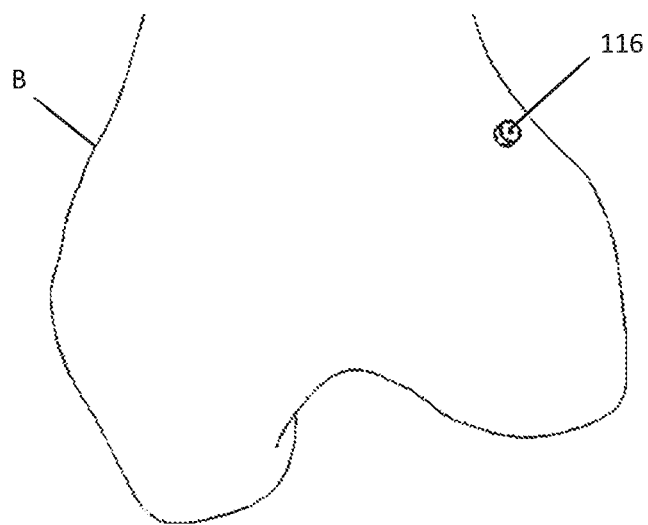
FIG. 3A depicts a placement of a first recovery marker on a bone in accordance with embodiments of the invention.

In a particular inventive embodiment, with respect to FIG. 3A, a bone is shown with a first recovery marker 116 installed in the bone B at a first location corresponding to step S110 of FIG. 1. Here, the point recovery marker 110 acts as the first recovery marker 116 installed on the bone, however it should be appreciated that the groove recovery marker 101 may be installed on the bone first and act as the first recovery marker 116 without deviating from the scope of the invention.

Figure 3B:
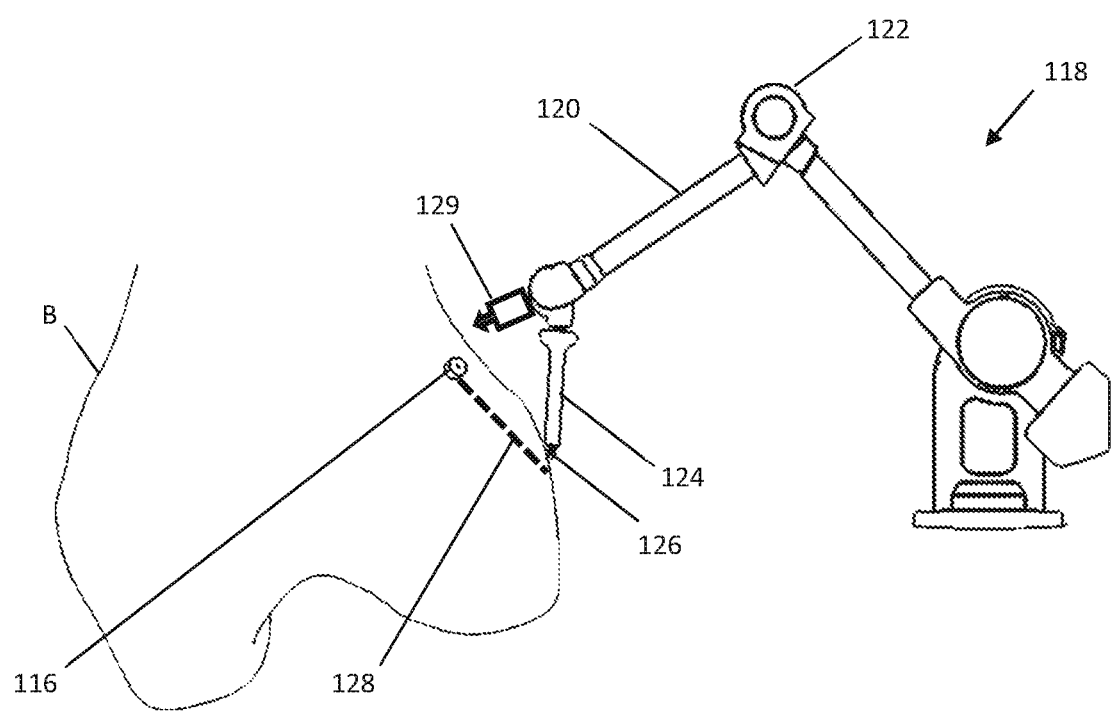
FIG. 3B depicts a placement of a first recovery marker and a process for calculating a distance on a bone from the first recovery marker in accordance with embodiments of the invention.

In a specific embodiment, with respect to FIG. 3B, a mechanical digitizer 118 is shown probing the bone B. The mechanical digitizer 118 includes articulating links 120 joined by joints 122, and a probe 124 having a probe tip 126 attached to a distal link of the digitizer 118. Each joint has encoders to determine at least one of a position and orientation of the probe tip 126 in three-dimensional space. In a specific embodiment, the mechanical digitizer is integrated to the base of a robotic arm and registered to the robotic arm as described in U.S. Pat. No. 6,033,415.

Corresponding with step S120 of FIG. 1, a user determines the position of the first recovery marker 116 by placing the probe tip 126 in the divot 112 of the point recovery marker 110 and recording the first recovery marker position. In other embodiments, if the groove recovery marker 101 is used as the first recovery marker 116, the user can slide the probe tip 126 along the length of the groove 106 to collect and record a series of points along the length of the groove recovery marker 101.

Corresponding with step S130 of FIG. 1, the user then navigates the surface of the exposed bone, B with the probe tip 126 around the first marker 116 as initially placed in FIG. 3A to search for an adequate position for a second recovery marker that satisfies the pre-determined distance, as shown in FIG. 3B as the dashed line 128. Corresponding to step S140 of FIG. 1, in real-time, a processor associated with at least one of a digitizer, a computer-assisted surgical device, or an optical tracking system calculates the distance between: the probe tip 126 of FIG. 3B as the user navigates the bone B; and the first recovery marker 116. Once the probe tip 126 is at, or beyond a pre-determined distance from the first marker 116, feedback is provided to the user (step S150 of FIG. 1). The user may navigate the probe tip 126 in any direction along the surface of the bone B to locate a position for a second recovery marker that satisfies the pre-determined distance. This is particularly advantageous for several reasons. First, the user no longer resorts to a ruler to adequately distance the two or more recovery markers. Second, the user may locate several different positions for a second recovery marker rapidly and can choose one location over another depending on several factors such as the surgeon's preference, the exposure of the bone, or where the surgical cutting tool is going to operate.

In specific inventive embodiments, to facilitate the calculation between the first recovery marker 116 and a potential position for a second recovery marker, a virtual sphere having a radius of the pre-determined distance 128 is utilized. For example, after the user collects a point or a series of point on a first recovery marker, the center of the virtual sphere is virtually superimposed at the collected point(s). As best seen in FIG. 3B, the user navigates the probe tip 126 on the bone B, the processor determines when the probe tip is at or crosses the boundary of the virtual sphere of which line 128 denotes a radius, which indicates that the probe tip 126 is at or beyond the pre-determined distance. As long as the probe tip 126 is at or beyond the virtual sphere boundary, the user is notified that a second recovery marker may be installed. In some inventive embodiments, a gimbal mounted laser 129 projects a spot or moving spot that defines a circle corresponding to the virtual sphere onto the surface of the bone B. In other inventive embodiments, a projector projects a circle directly on the bone B corresponding to the virtual sphere.

Figure 4A:
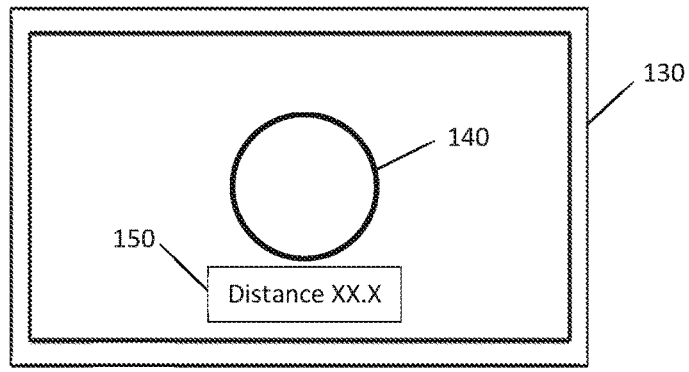
FIGS. 4A-4C depict several feedback mechanisms to notify a user when a tracked digitizer probe is at or beyond a pre-determined distance from a first recovery marker, where
Figure 4B:
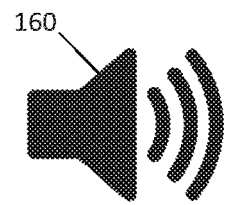
Figure 4C:
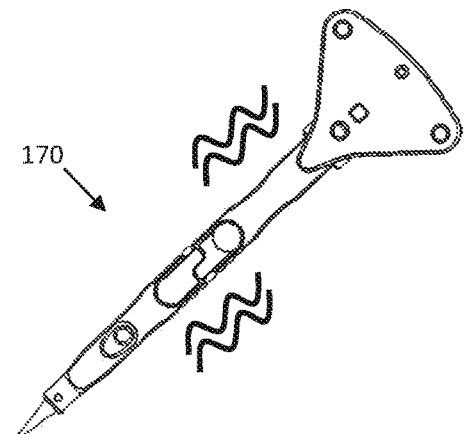

With reference to FIGS. 4A-4C, a feedback mechanism is provided to the user once the probe tip 126 is navigated to a distance at or beyond the pre-determined distance from the first recovery marker 116 (S150). The feedback mechanism notifies the user that the probe tip 126 is at a location on the bone B that satisfies the pre-determined distance. Accordingly, the user may then choose to install a second recovery marker at this second position. In one inventive embodiment, with reference to FIG. 4A, the feedback is provided in the form of a visual signal 140 displayed on a monitor 130. The visual signal 140 may include a variety of lights, a written notification, a symbol notification, or any indicia equivalent thereof. In a specific embodiment, the monitor 130 may also include a distance calculator visual display 150. The distance calculator visual display 150 may calculate and visually notify the user of the calculated distance between two or more given points.

In a specific inventive embodiment, with reference to FIG. 4B, the feedback is provided in the form of an acoustic signal 160. The acoustic signal 160 may further include a variety of audible notification sounds illustrative including a beeping sound, a vocal sound, or a combination thereof.

In another inventive embodiment, with reference to FIG. 4C, the feedback is provided in the form of a haptic signal 170. The haptic signal 170 may be in any form of a vibration or other imposed force on the user. Here, it should be appreciated that the feedback system may be in the form of any of acoustic, motion, visual signals, or a combination of any of them together. This is particularly advantageous as variety forms of notification can reduce errors in determination of the adequate distance between recovery markers. Also, any form of the feedback signals may be transient and fades away after the feedback mechanism notifies the user that the probe tip 126 is at a location on the bone B that satisfies the pre-determined distance 128. Likewise, the feedback signals may increase or decrease in strength as the user navigates the probe tip 126 closer to or farther away from the pre-determined distance, so as to essentially guide the user to an adequate location.

Figure 5:
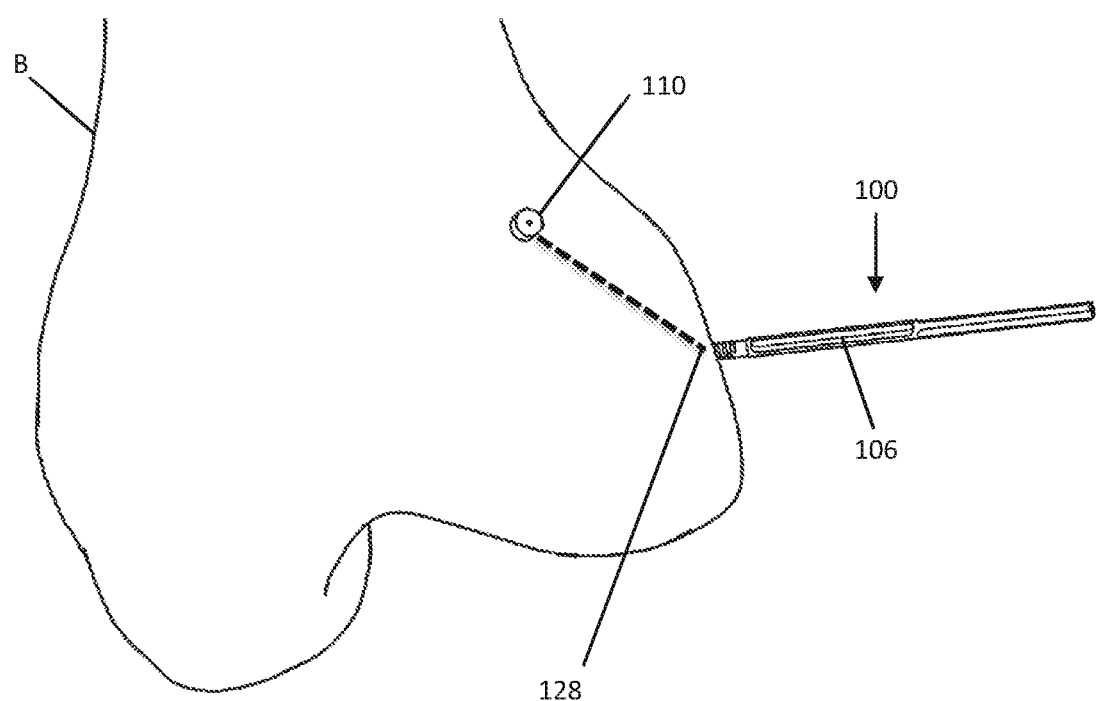
FIG. 5 depicts the placement of a second recovery marker installed at or beyond the pre-determined distance from a first recovery marker in accordance with embodiments of the invention.

With respect to FIG. 5, after the user locates a desired position for the second recovery marker in the form of groove recovery marker 101 that satisfies the pre-determined distance 128, the second recovery marker is installed (S160) where those portions of the second marker have the aforementioned properties as detailed with respect to FIG. 2B that depicts the groove recovery marker 101. A distal end of a passive digitizer arm, a tracked probe, or a distal end of a robotic surgical system is used to digitize several points (e.g., 10 or more) along the groove 106 of the groove recovery marker 101 that is acting as the second recovery marker (S170). The user can simply slide the distal end or probe tip 126 along the groove 106 while the system (e.g., the computer-assisted surgical system, a mechanical digitizer system, or a tracking system) acquires the several points during the sliding action.

After the recovery markers 116 and 101 are digitized, the user can perform an initial registration on the bone using methods known in the art such as point-to-surface registration. If bone motion occurs after the initial registration, the user can simply re-digitize the first recovery marker and second recovery marker to re-register the bone within the desired accuracy. Additionally, this same procedure may be used to re-register the bone following a relative movement between a 6-DOF tracking device and the bone. As a result, a surgical procedure previously ceased do to loss of registration can be resumed.

It should be appreciated that although a point recovery marker and a groove recovery marker were described herein with respect to the drawings, embodiments of the inventive method may be readily adapted for other configurations of recovery markers. For example, three individual point recovery markers 110 may be used to re-register the bone rather than using a point recovery marker and groove recovery marker. All three individual point recovery markers 100 may be distanced the appropriate distance apart from one other to achieve re-registration within a desired accuracy using the same method as described herein. In another example, two individual point recovery markers 110 may be used, with one or more additional points collected directly on the bone, where the two individual point recovery markers 110 are appropriately distanced using the methods described herein. Finally, the recovery markers may have a configuration as described in U.S. Pat. No. 6,430,434.

Embodiments of the present invention are advantageous because a digitizer can precisely and accurately determine the distance and location of a second position relative to a first location, as opposed to use of less accurate methods illustratively including rulers. Another advantage of the present invention is the amount of time that a user will save while performing the surgery. Usually, use of conventional methods including a physical ruler or guessing a position for the second recovery marker is time consuming as the user is not able to find the accurate location with ease. Therefore, the present method is more accurate and efficient compared to those conventional methods.

Figure 6:
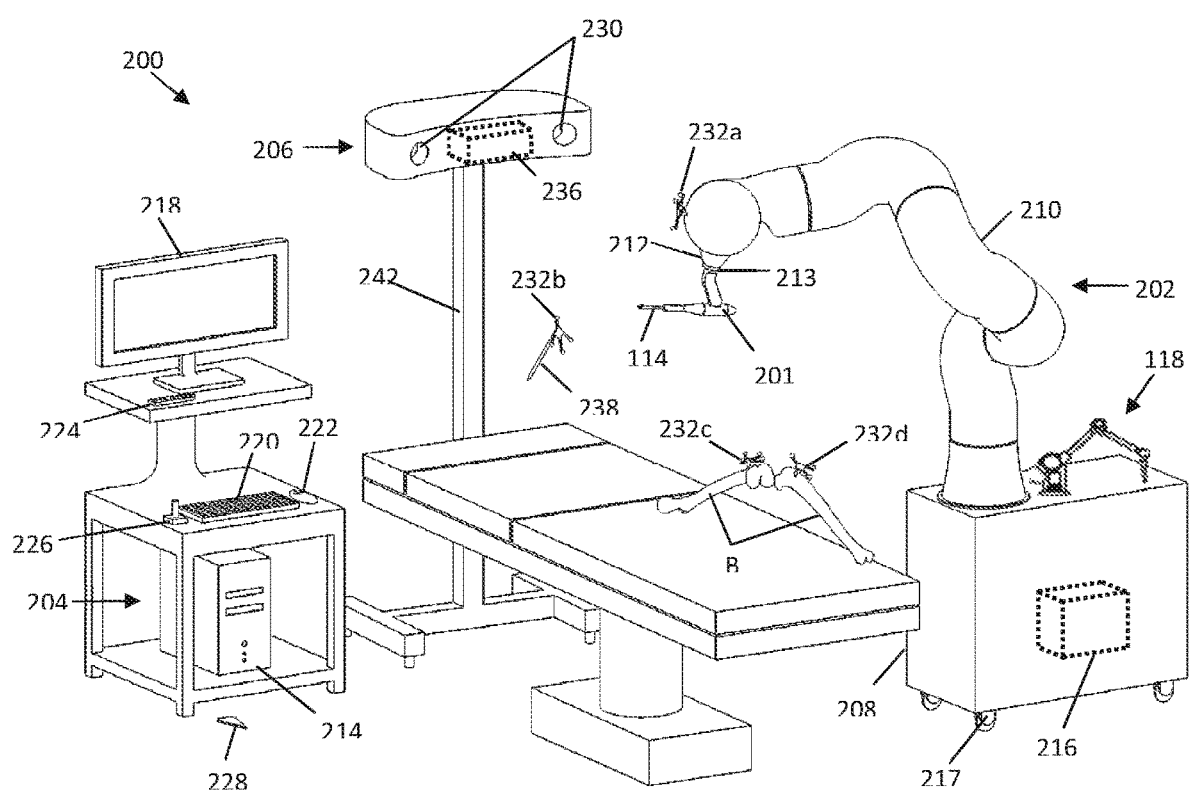
FIG. 6 illustrates a surgical system in the context of an operating room (OR) in accordance with embodiments of the invention

With reference to FIG. 6, an embodiment of a robotic surgical system is shown generally at 200 capable of implementing embodiments of the inventive method for installing recovery markers on a bone prior to surgery to permit bone re-registration during a surgical procedure or a cessation therein due to a loss of positional registry and is shown in the context of an operating room (OR). The surgical system 200 generally includes a surgical robot 202, a mechanical digitizer 118, a computing system 204, and optionally includes a tracking system 206. The surgical robot 202 may also have the capabilities of the mechanical digitizer 118 directly, where the mechanical digitizer 118 is no longer needed. A gimbal mounted laser 129 is optionally present in system 200 per FIG. 3B, but omitted for visual clarity from FIG. 6.

The surgical robot 202 may include a movable base 208, a manipulator arm 210 connected to the base 208, an end-effector flange 212 located at a distal end of the manipulator arm 210, and an end-effector assembly 201 for holding and/or operating a tool 114 removably attached to the flange 212 by way of an end-effector mount 213. The base 208 in some inventive embodiments includes a set of wheels 217 to maneuver the base 208, which may be fixed into position using a braking mechanism such as a hydraulic brake. The manipulator arm 210 includes various joints and links to manipulate the tool 114 in various degrees of freedom. If the mechanical digitizer 118 is not present, the tool 114 may be fitted with the probe tip 126 to implement measurements for bone registration, otherwise the mechanical digitizer 118 may perform the digitization. The joints are illustratively prismatic, revolute, or a combination thereof.

The computing system 204 generally includes a planning computer 214; a device computer 216; an optional tracking computer 236 if a tracking system 206 is present; and peripheral devices. The planning computer 214, device computer 216, and tracking computer 236, may be separate entities, single units, or combinations thereof depending on the surgical system. The peripheral devices allow a user to interface with the surgical system components and may include: one or more user-interfaces, such as a display or monitor 218; and user-input mechanisms, such as a keyboard 220, mouse 222, pendent 224, joystick 226, foot pedal 228, or the monitor 218 in some inventive embodiments have touchscreen capabilities.

The planning computer 214 contains hardware (e.g., processors, controllers, and memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan includes operational data for modifying a volume of tissue that is defined relative to the anatomy, such as a set of points in a cut-file to autonomously modify the volume of bone, a set of virtual boundaries defined to haptically constrain a tool within the defined boundaries to modify the bone, a set of planes or drill holes to drill pins in the bone, or a graphically navigated set of instructions for modifying the tissue. The surgical plan data in some inventive embodiments also includes the pre-determined distanced for spacing the recovery markers, and/or instructions for the end-effector assembly 201 to control the tool 114 and to actuate the probe tip 126 to implement measurements for bone registration. The data generated from the planning computer 214 may be transferred to the device computer 216 and/or tracking computer 236 through a wired or wirelessly connection in the operating room (OR); or transferred via a non-transient data storage medium (e.g., a compact disc (CD), a portable universal serial bus (USB) drive) if the planning computer 214 is located outside the OR.

The device computer 216 in some inventive embodiments is housed in the moveable base 208 and contain hardware, software, data and utilities that are preferably dedicated to the operation of the surgical device 202. This may include surgical device control, robotic manipulator control, the processing of kinematic and inverse kinematic data, the execution of registration algorithms, the execution of calibration routines, the execution of surgical plan data, coordinate transformation processing, providing workflow instructions to a user, and utilizing position and orientation (POSE) data from the tracking system 206.

The optional tracking system 206 of the surgical system 200 includes two or more optical receivers 230 to detect the position of fiducial markers (e.g., retroreflective spheres, active light emitting diodes (LEDs)) uniquely arranged on rigid bodies. The fiducial markers arranged on a rigid body are collectively referred to as a fiducial marker array 232, where each fiducial marker array 232 has a unique arrangement of fiducial markers, or a unique transmitting wavelength/frequency if the markers are active LEDs. An example of an optical tracking system is described in U.S. Pat. No. 6,061,644. The tracking system 206 may be built into a surgical light, located on a boom, a stand 242, or built into the walls or ceilings of the OR. The tracking system computer 236 may include tracking hardware, software, data and utilities to determine the POSE of objects (e.g., bones B, surgical device 204) in a local or global coordinate frame. The POSE of the objects is collectively referred to herein as POSE data, where this POSE data may be communicated to the device computer 216 through a wired or wireless connection. Alternatively, the device computer 216 may determine the POSE data using the position of the fiducial markers detected from the optical receivers 230 directly.

The POSE data is determined using the position data detected from the optical receivers 230 and operations/processes such as image processing, image filtering, triangulation algorithms, geometric relationship processing, registration algorithms, calibration algorithms, and coordinate transformation processing. For example, the POSE of a digitizer probe 238 with an attached probe fiducial marker array 232b may be calibrated such that the probe tip is continuously known as described in U.S. Pat. No. 7,043,961. The POSE of the tool tip or tool axis of the tool 114 may be known with respect to a device fiducial marker array 232a using a calibration method as described in U.S. Prov. Pat. App. 62/128,857. The device fiducial marker 232a is depicted on the manipulator arm 210 but may also be positioned on the base 208 or the end-effector assembly 201. Registration algorithms may be executed to determine the POSE and coordinate transforms between a bone B, a fiducial marker array 232c or 232d, and a surgical plan, using the registration methods described in U.S. Pat. Nos. 6,033,415, and 8,287,522.

Upon assembly of the device tracking array 232a to the surgical robot 202 prior to surgery, the POSE's of the coordinate systems, 232a and the end effector tool 114, are fixed relative to each other and stored in memory to accurately track the end effector tool 114 during the surgery (see for example U.S. Patent Publication 20140039517 A1) relative to the bone anatomy (e.g., bones B). The POSE data may be used by the computing system 204 during the procedure to update the bone and surgical plan coordinate transforms so the surgical robot 202 can accurately execute the surgical plan in the event any bone motion occurs. However, if there is unintentional movement between the fiducial marker arrays (232c, 232d) and the bone B after initially registering the bone B, then the bone needs to be re-registered to re-establish the coordinate systems between the fiducial marker arrays (232c, 232d) and the bone B. It should be appreciated that in certain embodiments, other tracking systems may be incorporated with the surgical system 200 such as an electromagnetic field tracking system or a 6-DOF mechanical tracking system. An example of a 6-DOF mechanical tracking system is described in U.S. Pat. No. 6,322,567. In a particular inventive embodiment, the surgical system 200 does not include a tracking system 206, but instead employs a bone fixation and monitoring system that fixes the bone directly to the surgical robot 202 and monitors bone movement as described in U.S. Pat. No. 5,086,401.

Other Embodiments

Patents and publications detailed herein are representative of the skill in art at the time of the present invention. These references are hereby incorporated by reference to the same extent as if each patent or publication was specifically and individually incorporated by reference.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method of preparing a bone for re-registration prior to robotic surgery, comprising:
installing a first recovery marker on the bone;
digitizing a first position of said first recovery marker with a digitizer probe having a probe tip;
navigating along a surface of the bone with said probe tip in various degrees of freedom to search for a plurality of positions to place a second recovery marker on the bone;
calculating with a processor a distance between said first recovery marker and said probe tip;
notifying a user when said processor calculates that a probe tip position of said probe tip is at or beyond a pre-determined distance from said first recovery marker to locate the plurality of positions to place the second recovery marker on the bone;
installing a second recovery marker on the bone at one of the plurality of positions at or beyond the pre-determined distance; and
digitizing a second position of said recovery marker to permit bone re-registration using said first recovery marker and said second recovery marker to prepare the bone for re-registration prior to the robotic surgery.

2. The method of claim 1 further comprising determining at least one of a position or orientation of at least a portion of said first recovery marker and said second recovery marker.

3. The method of claim 2 wherein said digitizing step is accomplished with a measurement system that is at least one of an electro-mechanical sensor arm, an optical tracking system with an optically tracked probe, an electro-magnetic tracking system, an ultrasound tracking system, or an imaging system, (e.g., computed tomography (CT), X-ray, fluoroscopy, ultrasound, or magnetic resonance imaging (MRI)).

4. The method of claim 3 wherein said imaging system is at least one of computed tomography (CT), X-ray, fluoroscopy, ultrasound, or magnetic resonance imaging (MRI).

5. The method of claim 1 wherein the pre-determined distance resolves the motion of the bone or a targeted region of the bone in 6-DOF (degrees of freedom).

6. The method of claim 1 wherein the surgical procedure is computer-assisted total joint replacement (TJR) surgery.

7. The method of claim 1 wherein the first position and the second position are digitized as a collection, recordation, or measurement of one or more physical coordinates in three-dimensional space.

8. The method of claim 1 wherein at least one of said first recovery marker or said second recovery marker further comprises a divot.

9. The method of claim 1 wherein said first recovery marker or said second recovery marker is a groove recovery marker, where the groove recovery marker further comprises a bone engaging portion, a proximal portion for engaging a driver tool, and a groove between the bone engaging portion and the proximal portion, where the groove facilitates the collection of a series of points along the length of the groove.

10. The method of claim 1 wherein said digitizing step is conducted with a mechanical digitizer that is integrated to a base of a robotic arm for a robotic surgical system to perform the surgical procedure on the bone.

11. The method of claim 1 further comprising a user navigating said probe tip in any direction along the surface of the bone to locate a position for said second recovery marker that satisfies the pre-determined distance.

12. The method of claim 1 further comprising mapping a virtual sphere having a radius of the pre-determined distance, where a user collects a point or a series of points on said first recovery marker, and a center of the virtual sphere is virtually superimpose at the collected point(s); and
notifying the user when the probe tip is at or crosses a boundary of the virtual sphere as a place where said second recovery marker may be installed in the bone.

13. The method of claim 1 further comprising alerting via a feedback mechanism when said probe tip is navigated to a distance at or beyond the pre-determined distance from said first recovery marker.

14. The method of claim 13 wherein the feedback mechanism provides feedback in the form of a visual signal displayed on a monitor.

15. The method of claim 14 wherein the monitor displays a distance calculator.

16. The method of claim 13 wherein the feedback mechanism is in the form of an acoustic signal or haptic signal.

17. The method of claim 1 further comprising projecting a laser light spot onto the bone, said laser light spot indicative of the predetermined distance.

18. The method of claim 1 wherein the pre-determined distance is proportional to a level of accuracy required for the bone re-registration.

19. The method of claim 1 wherein said calculating step is accomplished in real-time.

20. A system for implementing the method of re-registration of a bone during a surgical procedure of claim 1, said system comprising:
a robot configured with said digitizer probe to implement measurements for bone registration; and
one or more computers having one or more processors for calculating the distance between the probe tip and the first recovery marker and for locating the plurality of positions at or beyond the pre-determined distance.

* * * * *